United States Patent [19]

Clark

[11] 4,332,804
[45] Jun. 1, 1982

[54] 9-[2-(3-INDOLYL)ETHYL]-1OXA-4,9-DIAZASPIRO[5.5]UNDECAN-3-ONES

[75] Inventor: Robin D. Clark, Palo Alto, Calif.

[73] Assignee: Syntex (U.S.A.) Inc., Palo Alto, Calif.

[21] Appl. No.: 246,459

[22] Filed: Mar. 23, 1981

[51] Int. Cl.³ ............................................. A61K 27/00
[52] U.S. Cl. ................... 424/248.57; 544/71;
    546/16; 546/207; 546/216; 546/221
[58] Field of Search .................... 544/71; 424/248.57

[56] References Cited

U.S. PATENT DOCUMENTS

| | | | |
|---|---|---|---|
| 3,481,942 | 12/1969 | Loev | 546/19 |
| 3,574,204 | 4/1971 | Nakanishi et al. | 546/19 |
| 3,720,670 | 3/1973 | Nakanishi et al. | 544/71 |
| 3,723,442 | 3/1973 | Nakanishi et al. | 544/71 |

OTHER PUBLICATIONS

Maillard et al., Chimie Ther. No. 4 (Jul.-Aug. 1973), pp. 393–397.

*Primary Examiner*—Ethel G. Love
*Attorney, Agent, or Firm*—Annette M. Moore; Tom M. Moran; Alan M. Krubiner

[57] ABSTRACT

Compounds useful in the prevention and/or treatment of hypertension, congestive heart failure, arrhythmia, migraine, vasospastic disorders, and asthma are represented by the formula

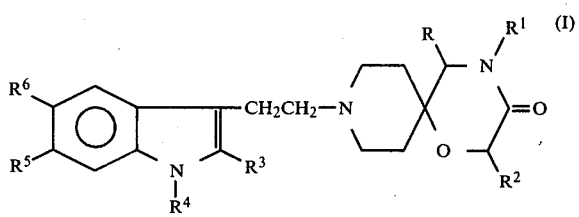

wherein:
  R, $R^1$, $R^2$, $R^3$, and $R^4$ are independently hydrogen or lower alkyl of one to four carbon atoms; and
  $R^5$ and $R^6$ are independently hydrogen, lower alkyl of one to four carbon atoms or lower alkoxy of one to four carbon atoms; and
  the pharmaceutically acceptable acid addition salts thereof.

20 Claims, No Drawings

9-[2-(3-INDOLYL)ETHYL]-1OXA-4,9-DIAZAS-PIRO[5.5]UNDECAN-3-ONES

BACKGROUND OF THE INVENTION

Field of the Invention

This invention relates to 9-[2-(3-indolyl)ethyl]-1-oxa-4,9-diazaspiro[5.5]undecan-3-ones and the pharmaceutically acceptable acid addition salts thereof which are useful in the prevention and/or treatment of hypertension, congestive heart failure, arrhythmia, edema, migraine, vasospastic disorders, and asthma. The invention also relates to a pharmaceutically acceptable composition containing an effective amount of at least one of the compounds in combination with a suitable excipient, the composition being useful for the prevention and/or treatment of hypertension, congestive heart failure, arrhythmia, migraine, vasospastic disorders, and asthma in mammals. The invention also relates to a process for making the compounds of the invention.

Related Disclosures

It is known that compounds of the formula

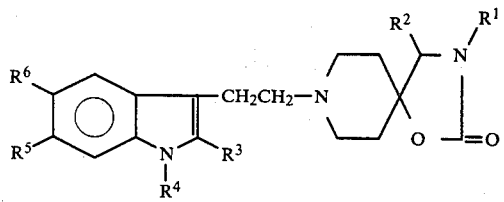

wherein $R^1$, $R^2$, $R^3$ and $R^4$ are, i.a., independently hydrogen or alkyl of one to six carbon atoms and $R^5$ and $R^6$ are, i.a., independently hydrogen, alkyl or one to six carbon atoms, or alkoxy of one to six carbon atoms exhibit antihypertensive, diuretic, antihistime, antiallergic and bronchodilating activity as well as are useful in the treatment of migraine and vasospastic disorders. See U.S. Pat. No. 4,255,432 and Chimie Therapeutique, Nov.-Dec. 1972, No. 6, pp. 458-466. A novel class of compounds has now been prepared which are more active than the compounds of the related disclosures.

SUMMARY OF THE INVENTION

The first aspect of this invention is the group of compounds represented by the formula

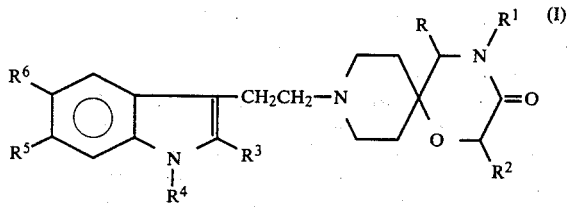

wherein:
R, $R^1$, $R^2$, $R^3$, and $R^4$ are independently hydrogen or lower alkyl of one to four carbon atoms; and
$R^5$ and $R^6$ are independently hydrogen, lower alkyl of one to four carbon atoms or lower alkoxy of one to four carbon atoms; and
the pharmaceutically acceptable acid addition salts thereof.

Another aspect of the invention is a composition useful in the prevention and/or treatment of hypertension, congestive heart failure, arrhythmia, migraine, vasospastic disorders and asthma in mammals which composition comprises an effective amount of at least one compound chosen from those represented by formula (I) above or a pharmaceutically acceptable acid addition salt thereof and a pharmaceutically suitable excipient.

Still another aspect of the invention is a method for preventing and/or treating hypertension, congestive heart failure, arrhythmia, migraine, vasospastic disorders and asthma in mammals which comprises administering an effective amount of at least one compound chosen from those represented by formula (I) above.

Still another aspect of the invention is a process for preparing a compound of formula (I) above which comprises reacting a compound of the formula

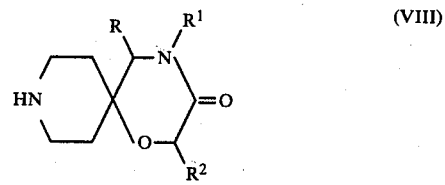

wherein:
R, $R^1$, and $R^2$ are as defined above with a suitable indolylethyl halide of the formula

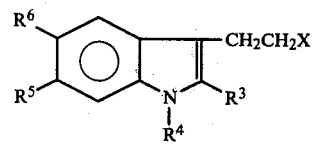

wherein: $R^3$, $R^4$, $R^5$, and $R^6$ are as defined above and X is a halide, e.g., chloro or bromo.

DETAILED DESCRIPTION AND PREFERRED EMBODIMENT

The broadest aspect of the present invention is the group of compounds represented by the formula

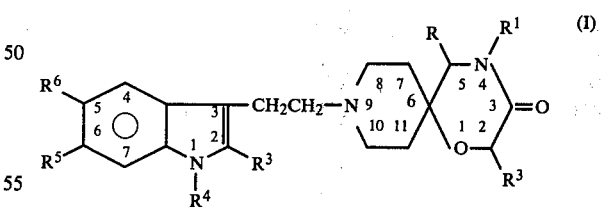

wherein:
R, $R^1$, $R^2$, $R^3$, and $R^4$ are independently hydrogen or lower alkyl of one to four carbon atoms; and
$R^5$ and $R^6$ are independently hydrogen, lower alkyl of one to four carbon atoms, or lower alkoxy of one to four carbon atoms; and
the pharmaceutically acceptable acid addition salts thereof.

A preferred group of compounds of formula (I) is that wherein R is lower alkyl and $R^1$, $R^2$, $R^3$, $R^4$, $R^5$ and $R^6$ are hydrogen, the most preferred group being wherein R is methyl or ethyl and the pharmaceutically acceptable acid addition salts thereof.

Another preferred group of compounds of formula (I) is that in which all R's are each hydrogen, namely, 9-[2-(3-indolyl)ethyl]-1-oxa-4,9-diazaspiro-[5.5]undecan-3-one and the pharmaceutically acceptable acid addition salts thereof.

As used in the specification and the appended claims, unless specified to the contrary, the following terms have the meaning indicated. The term "lower alkyl" refers to a straight or branched chain monovalent substituent consisting solely of carbon and hydrogen, containing no unsaturation and having from one to four carbon atoms. Examples of lower alkyl groups are methyl, ethyl, i-propyl and t-butyl. The term "lower alkoxy" refers to a monovalent substituent containing oxygen and of the formula "lower alkyl-O-" wherein lower alkyl is as defined above. Examples of lower alkoxy groups are methoxy, ethoxy, n-propoxy and i-butoxy. The term "pharmaceutically acceptable acid addition salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid; or organic acids such as acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The compounds of the present invention are named according to the IUPAC nomenclature system. The locants for the substituents on the ring systems of the compounds of the instant invention are as depicted above.

Certain compounds of formula (I) wherein R and $R^1$ are lower alkyl may have geometric (cis and trans) isomers. The geometric isomers may be separated by various methods, for example, selective crystallization and column chromatography. Alternatively, where appropriate, the intermediates of formula (VIII) (infra) may be separated and converted to the final cis or trans isomers of compounds of formula (I). Both geometric isomers as well as mixtures thereof are intended to be included within the scope of the present invention.

Compounds of formula (I) also exist as optical isomers because the spiral ring group does not possess a plane of symmetry. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form but to encompass the individual optical isomers of the subject compounds.

If desired, racemic intermediates of formula (VIII) (infra) or final products prepared herein may be resolved into their optical antipodes by conventional resolution means known per se, for example, by the separation (e.g., fractional crystallization) of the diastereomeric salts formed by reaction of, e.g., racemic compounds of formula (I) or the intermediate of formula (VIII) (infra) with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acids, and the like. The separated pure diastereomeric salts may then be cleaved by standard means to afford the respective optical isomers of the compounds of formula (I) or the intermediate of formula (VIII) (infra).

ADMINISTRATION AND FORMULATION

Another aspect of the present invention relates to pharmaceutical compositions useful in the prevention and/or treatment of hypertension, congestive heart failure, arrhythmia, migraine, vasospastic disorders, and asthma, particularly in the prevention and/or treatment of hypertension in a mammalian subject comprising a compound of formula (I), or a pharmaceutically acceptable acid addition salt thereof, in admixture with a pharmaceutically acceptable non-toxic carrier. Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Suitable pharmaceutical carriers and their formulations are described in "Remington's Pharmaceutical Sciences" by E. W. Martin. Such compositions will, in any event, contain a therapeutically effective amount of the active compound together with a suitable amount of carrier so as to prepare the proper dosage form for proper administration to the subject. Thus, the level of the drug in the formulation can vary from 5 percent weight (%W) to 95%W of the drug based on the total formulation and about 5%W to 95%W excipient. Preferably the drug is present at a level of 10%W to 70%W.

Another aspect of the present invention relates to a method for preventing and/or treating hypertension, congestive heart failure, arrhythmia, migraine, vasospastic disorders and asthma in a mammalian subject comprising administering a therapeutically effective amount of a compound of formula (I), or a pharmaceutically acceptable acid addition salt thereof.

In the practice of the above described methods of the present invention a therapeutically effective amount of the compound of formula (I) or a pharmaceutical composition containing same is administered via any of the usual and acceptable methods known in the art, either singly or in combination with another compound or compounds of the present invention or other pharmaceutical agents. These compounds or compositions can thus be administered orally, systemically (i.e., intranasally, or by suppository) or parenterally (i.e., intramuscularly, subcutaneously and intravenously), and can be administered either in the form of solid or liquid dosages including tablets, solutions, suspensions, aerosols, and the like, as discussed in more detail hereinabove.

The formulation can be administered in a single unit dosage form for continuous treatment or prevention or in a single unit dosage form ad libitum when relief of symptoms is specifically required.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount ranges from about 0.01 to about 5 mg./kg. body weight per day and preferably, for example, for antihypertensive use, from about 1 to about 3 mg./kg. body weight per day. In alternative terms, for an average adult human subject, a therapeutically effective amount in accordance herewith would be, in preferred embodiments from about 7 mg. to about 120 mg. per day per subject.

PROCESS OF THE INVENTION

Compounds of formula (I) are prepared by the reaction sequence shown below.

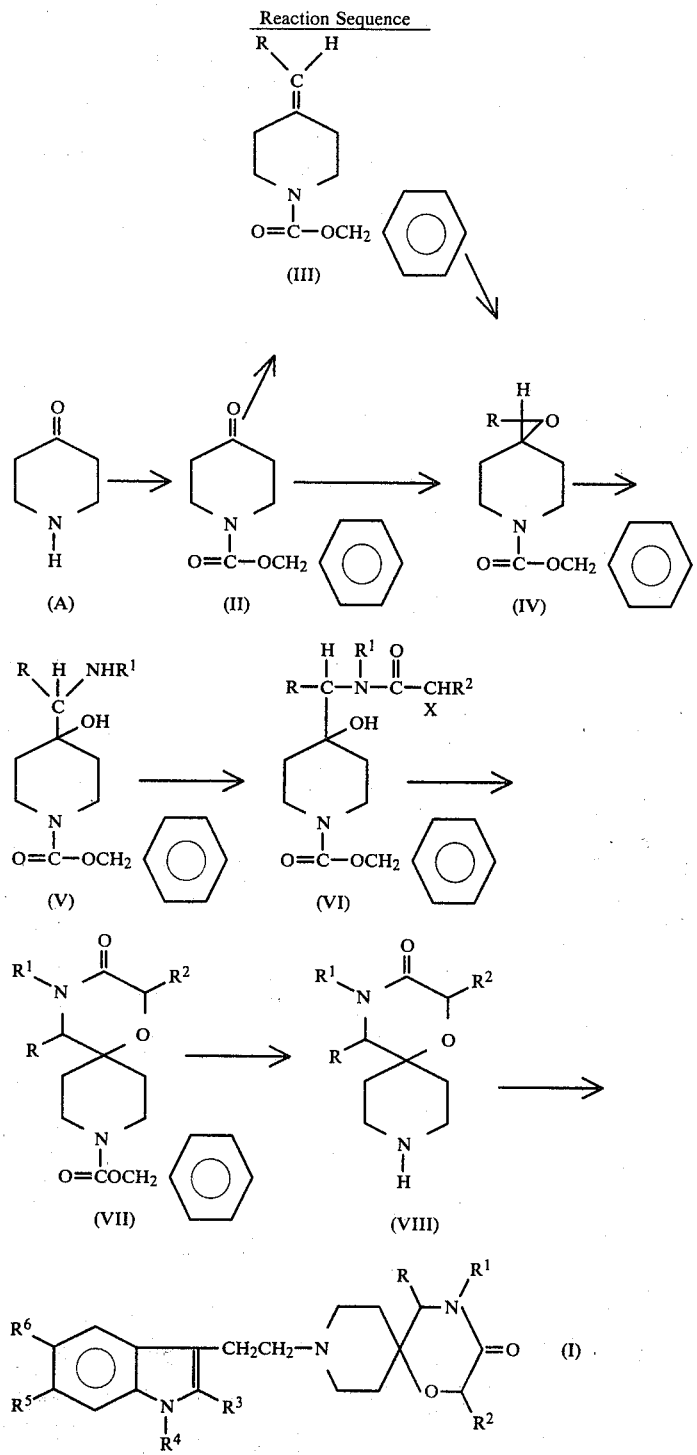

wherein R, $R^1$, $R^2$, $R^3$, $R^4$, $R^5$ and $R^6$ are as defined above and X is chloro or iodo.

In the above sequence, 4-piperidone(A), available from Aldrich Chemical Co., is reacted with benzyl chloroformate, also available from Aldrich Chemical Co., by the method described in *Organic Chemistry*, by Robert T. Morrison and Robert N. Boyd, 2nd Edition, Ch. 37, p. 1112 to yield the N-protected-4-piperidone of formula (II). Typically, the reaction is carried out in a solvent such as water and is cooled to a temperature of about 0° C. to about 25° C., preferably from about 5° C. to about 15° C. for 3 hours to 24 hours, preferably 6 hours to 12 hours. The 4-piperidone is in a molar ratio of 0.7 to 0.8 mole to 1 mole of benzyl chloroformate, particularly in a molar ratio of 0.75 mole of 4-piperidone to 1 mole of benzyl chloroformate.

The N-protected piperidine epoxide of formula (IV) wherein R is hydrogen is prepared by the method described in J. Am. Chem. Soc., 81, 1353 (1965). N-protected piperidone, dispersed or dissolved in a suitable liquid such as dimethyl sulfoxide, tetrahydrofuran and the like is reacted with an ylid formed by the reaction of trimethyl sulfonium or trimethyl sulfoxonium iodide with an alkali metal hydride such as sodium hydride. Typically, the reactants, in a molar ratio of from 1 to 2 moles, preferably from 1.3 to 1.6 moles of ylid to 1 mole of N-protected-4-piperidone, are stirred at a temperature of between 0° C. to 30° C., preferably at room temperature for about 10 hours to 24 hours, preferably for about 12 hours to 18 hours. This is followed by heating at 40° C. to about 100° C., preferably from about 50° C. to 60° C., for 15 minutes to about 2 hours, preferably for about 45 minutes to about 1.5 hours.

The epoxides of formula (IV) wherein R is lower alkyl are prepared by first preparing the olefin of formula (III) then epoxidizing the olefin by methods well known in the art such as by the catalytic oxidation of the C—C double bond with air or by peroxidation of the C—C double bond with a peroxy acid such as peroxybenzoic acid. The compounds of formula (III) are prepared by the well known Wittig reaction in which N-protected piperidone is reacted with a methylenetriphenylphosphorane ylid of the formula $Ph_3P=CHR$ wherein R is as defined above. The ylid is prepared by reacting triphenylphosphine with an $RCH_2$ halide wherein R is as defined above followed by reaction with an organolithium compound such as phenyllithium or n-butyllithium. The reaction conditions for the preparation of the ylid and the olefin are thoroughly discussed in "The Wittig Reaction" by Adalbert Maercker in *Organic Reaction* V. 14, Ch. 3, p. 270 (1965).

The epoxide ring of compounds of formula (IV) is readily opened at elevated temperatures by any $R^1$-substituted amine wherein $R^1$ is as defined above forming 1-carbobenzoxy-4-hydroxy-4-($R^1$-aminomethyl)piperidine of formula (V). Typically, the reactants are heated at a temperature of between about 75° C. to about 175° C., preferably from about 100° C. to about 125° C. for about 3 hours to about 24 hours, preferably for about 3 hours to about 6 hours. The reaction is typically conducted in a solution of the $R^1$-substituted amine in an alcohol such as ammonia in methanol at a molar ratio of N-protected piperidine epoxide to amine of 1 mole to 50 moles, preferably of 1 mole to 20 moles.

The hydroxy amine compounds of formula (V) are reacted with an α-chloroacid chlorides such as α-chloroacetyl chloride, α-chloropropionylchloride, α-chloro-n-butryl chloride and the like in a polar aprotic solvent such as ethyl acetate, tetrahydrofuran, dimethyl formamide and the like optionally followed by reaction with an alkali metal iodide such as sodium iodide to yield compounds of formula (VI) wherein X is chloro or iodo. The reaction is run in the presence of a suitable acid acceptor such as trimethylamine, triethylamine, an alkali metal carbonate such as sodium or potassium carbonate and the like at a temperature from about 0° C. to about 25° C., preferably from about 5° C. to about 10° C.

The α-chloroacid chlorides which are not readily available may be prepared by conventional methods such as the Hell-Volhard-Zelinsky Reaction in which the appropriate acid is reacted with chlorine in the presence of phosphorus. See, for example, *Organic Chemistry* by Robert T. Morrison and Robert N. Boyd, 2nd Edition, Ch. 18, p. 604 and Chem. Revs. 7, 180 (1930).

Cyclization of compounds of formula (VI) is carried out by contacting compounds of formula (VI) with a strong base such as an alkali metal alkoxide dissolved in an alcohol (e.g. potassium t-butoxide in t-butyl alcohol) in a polar aprotic solvent such as tetrahydrafuran, dimethylformamide and the like. The mixture is refluxed for about 0.1 hour to about 1 hour, preferably for about 0.1 hour to about 0.2 hour.

The compounds of formula (VII) are treated with hydrogen bromide in acetic acid to remove the N-protecting group to yield compounds of formula (VIII).

The intermediate 3-(2-haloethyl)indoles are readily prepared by reacting a solution or dispersion of the unsubstituted or substituted-3-(2-hydroxyethyl)indole with a phosphorus trihalide, a triphenyl phosphine halogen adduct or a triphenoxyphosphorus alkyl halide. The reaction is typically carried out in an inert reaction medium such as dimethylformamide, diethylether and the like from about room temperature to about 100° C. using an excess of a halogenating agent, e.g., 1.1 to 3.0 times the molar equivalence of the hydroxyethylindole. The haloethylindole intermediate is preferably isolated before being used in the reaction with compounds of formula (VIII), the isolation being accomplished by conventional means.

The hydroxyethylindoles which are not readily available may be prepared by methods well known in the art. For example, when $R^3$ is lower alkyl and $R^5$ and/or $R^6$ are hydrogen, lower alkoxy, or lower alkyl, the substituted hydroxyethylindoles may be prepared by the methods described in U.S. Pat. No. 3,294,804 in which aniline or a substituted aniline is reacted with a halogenated ketoacid alkyl ester at a temperature of about 170° C. to about 190° C. for five to twenty minutes. The resultant indole acetic acid is reduced to the alcohol with lithium aluminium hydride.

The hydroxyethylindoles wherein $R^5$ and/or $R^6$ are lower alkyl and $R^3$ is hydrogen are obtained by the method described in J. Amer. Chem. Soc., 76, 2206 (1953) and U.S. Pat. No. 3,316,160 followed by reduction to the alcohol. The substituted phenylhydrazine is reacted with β-formylpropionic acid ester and then cyclized to the indole acetic acid. The indole acetic acid is reduced to the hydroxyethylindole by conventional means well known in the art such as with lithium aluminum hydride.

The phenylhydrazines which are not readily available may be prepared by diazotizing the appropriately substituted aniline with sodium nitrite and hydrochloric acid, then treating with sodium sulfite followed by treatment with sodium hydroxide as described in *Organic Synthesis*, 2nd Ed., coll. vol. 1, 442 (1941).

The hydroxyethylindoles wherein $R^4$ is lower alkyl may be prepared by alkylation with the appropriate alkyl halide, for example, methyl iodide, ethyl iodide and the like.

The compounds of the instant invention are prepared by treating the 3-(2-haloethyl)indole intermediate with the compound of formula (VIII) in the presence of the acid acceptor in an inert organic solvent such as dimethylformamide, tetrahydrofuran and the like at a temperature from about −10° C. to 120° C., preferably from about 50° C. to about 100° C. for about 6 hours to about 48 hours, preferably from about 16 hours to about 18 hours. Effective acid acceptors are organic bases such as trialkyl amines, e.g., trimethylamine, triethylamine and quinuclidine and inorganic bases such as alkali metal carbonates, for example, sodium carbonate or potassium carbonate and alkali metal hydroxide such as sodium hydroxide, potassium hydroxide and the like.

The compounds of formula (I) may be isolated as free bases, but it is more convenient to isolate the compounds of the instant invention as acid addition salts. These salts are prepared in the usual manner, i.e., by reaction of the free base with a suitable organic or inorganic acid, for example, one of the pharmaceutically acceptable acids described above. If desired, the salt can be readily converted to the free base by treatment with a base such as potassium or sodium carbonate or potassium or sodium hydroxide.

The following specific description is given to enable those skilled in the art to more clearly understand and practice the invention. It should not be considered as a limitation upon the scope of the invention but merely as being illustrative and representative thereof.

PREPARATION 1

(Preparation of compounds of formula (IV) wherein R is hydrogen)

In a 250 ml flask under argon was mixed 1.2 g mineral oil-free sodium hydride, 11 g trimethylsulfoxonium iodide and 60 ml dimethylsulfoxide. The mixture was stirred for two hours and then was added 9.32 g of N-carbobenzyloxy-4-piperidone, the stirring being continued at room temperature for 30 minutes, followed by 50° for one hour, then room temperature for 18 hours. The mixture was poured into 300 ml water and extracted with three 70 ml portions of diethyl ether. The combined diethyl ether extracts were washed with 50 ml water. Removal of solvent by evaporation afforded 3.8 g of crude 1-carbobenzoxypiperidin-4-epoxide.

PREPARATION 2

(Preparation of compounds of formula (IV) wherein R is lower alkyl)

(A) Butyl lithium (44 ml of 1.6 M in hexane) was added slowly to a stirred suspension of 27 g of (n-propyl)-triphenylphosphonium bromide in 350 ml of tetrahydrofuran and the resulting solution was refluxed for 1 hour. The mixture was cooled in an ice bath and 18 g of N-carbobenzyloxy-4-piperidone was added. After stirring at room temperature of 0.5 hour, the solution was refluxed for 2 hours. The cooled mixture was concentrated under reduced pressure, partitioned between ether and water, and the ether was dried (sodium sulfate) and evaporated. The residue was filtered through silica gel with 20% ethyl acetate-hexane to give 10 g of 1-carbobenzoxy-4,1'-epoxybutylpiperidine as a colorless oil.

(B) The above olefin (13.3 g) in 150 ml of chloroform at 50° C. was treated with 12 g of m-chloroperoxybenzoic acid and the resulting solution was kept at 5° C. for 20 hours. The chloroform was washed with 5% sodium hydroxide solution and evaporated to afford 14 grams of 1-carbobenzoxy-4,1'-epoxybutyl-piperidine as a colorless oil.

(C) Similarly, proceeding as in Part A and B above, substituting the appropriate R-triphenylphosphonium bromide for (n-propyl)triphenylphosphonium bromide the following compounds are prepared:
1-carbobenzoxy-4,1'-epoxyethylpiperidine, R is methyl;
1-carbobenzoxy-4,1'-epoxypropylpiperidine, R is ethyl;
1-carbobenzoxy-4,1'-epoxy-2-methylpropylpiperidine, R is i-propyl; and
1-carbobenzoxy-4,1'-epoxypentylpiperidine, R is n-butyl.

PREPARATION 3

(Preparation of compounds of formula (VI))

(A) A solution of 77 g of 1-carbobenzoxypiperidin-4-epoxide in 1 liter of 15% ammonia-methanol was heated in a steel bomb at 100° for 24 hours. The mixture was cooled and evaporated and the residue was dissolved in 600 ml of ethyl acetate. Water (500 ml) and 125 g of potassium carbonate were added and the two phase mixture was cooled to 5° C. and 35 ml of chloroacetyl chloride was slowly added. The ethyl acetate layer was separated and evaporated to a residue which was dissolved in 400 ml of acetone. Sodium iodide (75 g) was added and the solution was stirred for 12 hours at reflux. The solvent was evaporated and the residue was partitioned between water and ethyl acetate. The ethyl acetate was evaporated and the residue was filtered through 1.25 kg of silica gel with ethyl acetate eluent to afford 59.6 g of 1-carbobenzoxy-4-hydroxy-4-(1-iodoacetylamidomethyl)piperidine as a white solid; mp 115°–117° C.

(B) A solution of potassium t-butoxide (25 g) in t-butanol (600 ml) was refluxed while a solution of 1-carbobenzoxy-4-hydroxy-4-(1-iodoacetylamidomethyl)-piperidine (50 g) in tetrahydrofuran (300 ml) was slowly added. The mixture was neutralized with acetic acid, evaporated, dissolved in ethyl acetate and washed with water. Evaporation of the ethyl acetate left a residue which was triturated with ether to afford 90 g of solid. This material (70 g) was dissolved in 400 ml of 2 N HBr in acetic acid and stirred for 1 hour. The precipitate was filtered and washed with ether to give 70 g of the hydrobromide salt of 1-oxa-4,9-diazaspiro[5.5]undecan-3-one as a white solid; mp 200°–202° C.

(C) Similarly, proceeding as in Parts A and B above, but substituting methylamine, ethylamine, n-propylamine, and i-butylamine for ammonia, the following compounds are prepared:
4-methyl-1-oxa-4,9-diazaspiro[5.5]undecan-3-one;
4-ethyl-1-oxa-4,9-diazaspiro[5.5]undecan-3-one;
4-n-propyl-1-oxa-4,9-diazaspiro[5.5]undecan-3-one; and
4-i-butyl-1-oxa-4,9-diazaspiro[5.5]undecan-3-one.

(D) Similarly, proceeding as in Parts A and B above, but substituting the appropriate epoxide from Preparation 2 for 1-carbobenzoxypiperidin-4-epoxide, the following compounds are prepared:
5-methyl-1-oxa-4,9-diazaspira[5.5]-undecan-3-one;
5-ethyl-1-oxa-4,9-diazaspira[5.5]undecan-3-one;

5-i-propyl-1-oxa-4,9-diazaspira[5.5]undecan-3-one; and
5-n-butyl-1-oxa-4,9-diazaspira[5.5]undecan-3-one.

(E) Similarly, proceeding as in Parts A and B above, but substituting the appropriate epoxide from Preparation 2 for 1-carbobenzyloxypiperidin-4-epoxide and methylamine, ethylamine, i-propylamine and n-butylamine for ammonia, the following compounds are prepared:
4,5-dimethyl-1-oxa-4,9-diazaspiro[5.5]undecan-3-one;
4-ethyl-5-methyl-1-oxa-4,9-diazaspiro[5.5]undecan-3-one;
5-ethyl-4-methyl-1-oxa-4,9-diazaspiro[5.5]undecan-3-one;
5-methyl-4-i-propyl-1-oxa-4,9-diazaspiro[5.5]undecan-3-one; and
4-n-butyl-5-ethyl-1-oxa-4,9-diazaspiro[5.5]undecan-3-one.

(F) Similarly, proceeding as in Part A and B above, substituting α-chloropropionyl chloride, α-chlorobutryl chloride, and α-chlorohexanoyl chloride for α-chloroacetyl chloride, the following compounds are prepared:
2-methyl-1-oxa-4,9-diazaspiro[5.5]undecan-3-one;
2-ethyl-1-oxa-4,9-diazaspiro[5.5]undecan-3-one; and
2-i-butyl-1-oxa-4,9-diazaspiro[5.5]undecan-3-one.

(G) Similarly, proceeding as in Part A and B above, but substituting the appropriate amine for ammonia and the appropriate acid chloride for α-chloroacetyl chloride, the following compounds are prepared:
2,4-dimethyl-1-oxa-4,9-diazaspiro[5.5]undecan-3-one from methylamine and α-chloropropionyl chloride;
2-ethyl-4-methyl-1-oxa-4,9-diazaspiro[5.5]undecan-3-one from methylamine and α-chlorobutryl chloride;
2-i-propyl-4-methyl-1-oxa-4,9-diazaspiro[5.5]undecan-3-one from methylamine and β-methyl-α-chlorobutayl chloride; and
2-n-butyl-4-ethyl-1-oxa-4,9-diazaspiro[5.5]undecan-3-one from ethylamine and α-chlorohexanoyl chloride.

(H) Similarly, proceeding as in Parts A and B above, but substituting the appropriate epoxide from Preparation 2 for 1-carbobenzyloxy-piperidin-4-epoxide α-chloropropionyl chloride, α-chlorobutryl chloride, and α-chlorohexanoyl chloride for α-chloroacetyl chloride, the following compounds are prepared:
2,5-dimethyl-1-oxa-4,9-diazaspiro[5.5]undecan-3-one;
2-ethyl-5-methyl-1-oxa-4,9-diazaspiro[5.5]undecan-3-one;
2-methyl-5-i-propyl-1-oxa-4,9-diazaspiro[5.5]undecan-3-one; and
2-n-butyl-5-methyl-1-oxa-4,9-diazaspiro[5.5]undecan-3-one.

PREPARATION 4

To a mechanically stirred mixture of 31 g triphenylphosphine and 375 ml acetonitrile, 18.9 g bromine is added dropwise over 20 minutes. The mixture is stirred 20 minutes at 0° and the ice bath is removed. A solution of 17 g of (2-hydroxyethyl)indole in 150 ml acetonitrile is added over 30 minutes. After stirring 2 hours at room temperature the mixture is diluted with 1000 ml diethyl ether. The liquid is decanted from the precipitated orange oil. The residue is washed with an additional 500 ml diethyl ether. The volume of the ethereal extracts is reduced to about 60 ml and the solution is filtered through 150 g silica gel with diethyl ether. The solvent is removed to yield 3-(2-bromoethyl)indole, 22.5 g, white waxy solid, mp 57°-60°.

Similarly, proceeding as above, substituting the appropriate hydroxyethylindole for 3-(2-hydroxyethyl)indole, the following compounds are prepared:
3-(2-bromoethyl)-2-methylindole;
3-(2-bromoethyl)-1-methylindole;
3-(2-bromoethyl)-5-methoxyindole;
3-(2-bromoethyl)-5-n-butylindole; and
3-(2-bromoethyl)-6-methylindole.

EXAMPLE 1

(Preparation of compounds of formula (I))

(A) A solution of the hydrobromide salt of 1-oxa-4,9-diazaspiro[5.5]undecan-3-one (15 g) and 3-(2-bromoethyl)indole (13.5 g) in 75 ml of dimethylformamide and 20 ml of triethylamine was stirred at 65° C. for 16 hours. Water was added and the mixture was extracted with methylene chloride. The organic layer was extracted with 5% hydrochloric acid and the aqueous layer was made basic with ammonium hydroxide and extracted with methylene chloride. Evaporation left a residue which was chromatographed on silica gel with 10% methanol-methylene chloride to give 8.0 g of 9-[2-(3-indolyl)ethyl-]-1-oxa-4,9-diazaspiro[5.5] undecan-3-one as the free base, mp 48°-50° C. The free base was dissolved in methanol and acidified with methanolic hydrochloric acid. The precipitate was washed with ether to give 7 g of the hydrochloride salt of 9-[2-(3-indolyl)ethyl]-1-oxa-4,9-diazaspiro[5.5]undecan-3-one, mp 272°-275° C. (dec).

(B) Similarly, proceeding as in Part A above, but substituting the appropriate substituted-1-oxa-4,9-diazaspiro-[5.5]undecan-3-one from Preparation 3 for 1-oxa-4,9-diazaspiro[5.5]undecan-3-one, the following compounds are prepared:
9-[2-(3-indolyl)ethyl]-4-methyl-1-oxa-4,9-diazaspiro[5.5]undecan-3-one hydrochloride salt, m.p. 153°-155° C.;
9-[2-(3-indolyl)ethyl]-4-ethyl-1-oxa-4,9-diazaspiro[5.5]undecan-3-one hydrochloride salt, m.p. 280°-286° C.;
9-[2-(3-indolyl)ethyl]-4-n-propyl-1-oxa-4,9-diazaspiro[5.5]undecan-3-one hydrochloride salt, m.p. 217°-220° C.;
9-[2-(3-indolyl)ethyl]-4-i-butyl-1-oxa-4,9-diazaspiro[5.5]undecan-3-one;
9-[2-(3-indolyl)ethyl]-5-methyl-1-oxa-4,9-diazaspiro[5.5[undecan-3-one hydrochloride salt, m.p. 175°-177° C.;
9-[2-(3-indolyl)ethyl]-5-ethyl-1-oxa-4,9-diazaspiro[5.5]undecan-3-one hydrochloride salt, m.p. 240°-243° C.;
9-[2-(3-indolyl)ethyl]-5-i-propyl-1-oxa-4,9-diazaspiro[5.5]undecan-3-one;
9-[2-(3-indolyl)ethyl]-5-n-butyl-1-oxa-4,9-diazaspiro[5.5]undecan-3-one;
9-[2-(3-indolyl)ethyl]-4,5-dimethyl-1-oxa-4,9-diazaspiro[5.5]undecan-3-one hydrochloride salt, m.p. 210°-212° C.;
9-[2-(3-indolyl)ethyl]-4-ethyl-5-methyl-1-oxa-4,9-diazaspiro[5.5]undecan-3-one hydrochloride salt, m.p. 237°-238° C.;
9-[2-(3-indolyl)ethyl]-5-ethyl-4-methyl-1-oxa-4,9-diazaspiro[5.5]undecan-3-one hydrochloride salt, m.p. 266°-268° C.;
9-[2-(3-indolyl)ethyl]-5-methyl-4-i-propyl-1-oxa-4,9-diazaspiro[5.5]undecan-3-one;

9-[2-(3-indolyl)ethyl]-4-n-butyl-5-ethyl-1-oxa-4,9-diazaspiro[5.5]undecan-3-one;

9-[2-(3-indolyl)ethyl]-2-methyl-1-oxa-4,9-diazaspiro[5.5]undecan-3-one hydrochloride salt, m.p. 260°–263° C.;

9-[2-(3-indolyl)ethyl]-2-ethyl-1-oxa-4,9-diazaspiro[5.5]undecan-3-one hydrochloride salt, m.p. 236°–239° C.;

9-[2-(3-indolyl)ethyl]-2-i-butyl-1-oxa-4,9-diazaspiro[5.5]undecan-3-one;

9-[2-(3-indolyl)ethyl]-2,4-dimethyl-1-oxa-4,9-diazaspiro[5.5]undecan-3-one hydrochloride salt, m.p. 145°–147° C.;

9-[2-(3-indolyl)ethyl]-2-ethyl-4-methyl-1-oxa-4,9-diazaspiro[5.5]undecan-3-one, hydrochloride salt, 221°–222° C.;

9-[2-(3-indolyl)ethyl]-2-i-propyl-4-methyl-1-oxa-4,9-diazaspiro[5.5]undecan-3-one;

9-[2-(3-indolyl)ethyl]-2-n-butyl-4-ethyl-1-oxa-4,9-diazaspiro[5.5]undecan-3-one;

9-[2-(3-indolyl)ethyl]-2,5-dimethyl-1-oxa-4,9-diazaspiro[5.5]undecan-3-one;

9-[2-(3-indolyl)ethyl]-2-ethyl-5-methyl-1-oxa-4,9-diazaspiro[5.5]undecan-3-one;

9-[2-(3-indolyl)ethyl]-2-methyl-5-i-propyl-1-oxa-4,9-diazaspiro[5.5]undecan-3-one; and 9-[2-(3-indolyl)ethyl]-2-n-butyl-5-methyl-1-oxa-4,9-diazaspiro[5.5]undecan-3-one.

(C) Similarly, proceeding as in Part A above, but substituting the appropriate bromoethylindole from Preparation 4 for 3-(2-bromoethyl)indole, the following compounds are prepared:

9-[2-(2-methylindol-3-yl)ethyl]-1-oxa-4,9-diazaspiro[5.5]undecan-3-one;

9-[2-(1-methylindol-3-yl)ethyl]1-oxa-4,9-diazaspiro[5.5]undecan-3-one;

9-[2-(5-methoxyindol-3-yl)ethyl]-1-oxa-4,9-diazaspiro[5.5]undecan-3-one;

9-[2-(5-n-butylinol-3-yl)ethyl]-1-oxa-4,9-diazaspiro[5.5]undecan-3-one; and

9-[2-(6-methylindol-3-yl)ethyl]-1-oxa-4,9-diazaspiro[5.5]undecan-3-one.

EXAMPLE 2

8.0 g of 9-[2-(3-indolyl)ethyl]-1-oxa-4,9-diazaspiro[5.5]undecan-3-one was dissolved in methanol and acidified with methanolic hydrochloric acid. The precipitate was washed with ether to give 7.0 g of the hydrochloride salt of 9-[2-(3-indolyl)ethyl]-1-oxa-4,9-diazaspiro[5.5]undecan-3-one, m.p. 272°–275° C. (dec).

In similar manner, all compounds of formula (I) in base form can be converted to their pharmaceutically acceptable acid addition salts by treatment with the appropriate acid, for example, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methansulfonic acid, ethanesulfonic acid, p-toluenesulfonic acid and the like.

EXAMPLE 3

A solution of 3.5 g of 9-[2-(3-indolyl)ethyl]-1-oxa-4,9-diazaspiro[5.5]undecan-3-one hydrochloride salt in water (50 ml) was adjusted to pH 12 with ammonium hydroxide solution and extracted with methylene chloride. The methylene chloride was evaporated to afford 3 g of 9-[2-(3-indolyl)ethyl]-1-oxa-4,9-diazaspiro[5.5]undecan-3-one as the free base, mp 48°–50° C.

EXAMPLE 4

The following example illustrates the preparation of representative pharmaceutical formulations containing an active compound of Formula (I), e.g., 9-[2-(3-indolyl)ethyl]-1-oxa-4,9-diazaspiro[5.5]undecan-3-one.

| I.V. Formulation | | |
|---|---|---|
| Active compound | 0.14 | g |
| Propylene glycol | 20 | g |
| Polyethylene glycol 400 | 20 | g |
| Tween 80 | 1 | g |
| 0.9% Saline solution | 100 | ml |

The active compound is dissolved in propylene glycol, polyethylene glycol 400 and Tween 80. A sufficient quantity of 0.9% saline solution is then added with stirring to provide 100 ml of the I.V solution which is filtered through a 0.2 micron membrane filter and packaged under sterile conditions.

| TABLET FORMULATION | parts by weight |
|---|---|
| Active compound | 50.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol as the solvent. The formulation is then dried and formed into tablets (containing 50 mg of active compound) with an appropriate tabletting machine.

What is claimed is:

1. A compound of the formula

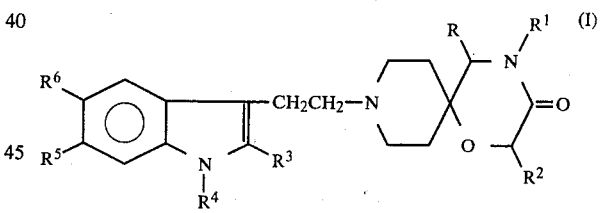

wherein:

R, $R^1$, $R^2$, $R^3$, and $R^4$ are independently hydrogen or lower alkyl of one to four carbon atoms; and $R^5$ and $R^6$ are independently hydrogen, lower alkyl of one to four carbon atoms or lower alkoxy of one to four carbon atoms; and the pharmaceutically acceptable acid addition salts thereof.

2. A compound of claim 1 wherein R, $R^1$, $R^2$, $R^3$, $R^4$, $R^5$, and $R^6$ are each hydrogen, which is 9-[2-(3-indolyl)ethyl]-1-oxa-4,9-diazaspiro-[5.5]undecan-3-one and the pharmaceutically acceptable acid addition salts thereof.

3. A compound of claim 1 wherein R is lower alkyl of one to four carbon atoms and $R^1$, $R^2$, $R^3$, $R^4$, $R^5$ and $R^6$ are each hydrogen.

4. A compound of claim 3 wherein R is methyl which is 5-methyl-9-[2-(3-indolyl)ethyl]-1-oxa-4,9-diazaspiro-[5.5]undecan-3-one and the pharmaceutically acceptable acid addition salts thereof.

5. A compound of claim 3 wherein R is ethyl which is 5-ethyl-9-[2-(3-indolyl)ethyl]-1-oxa-4,5-diazaspiro-

[5.5]undecan-3-one and the pharmaceutically acceptable acid addition salts thereof.

6. A compound of claim 3 wherein R is n-propyl which is 5-n-propyl-9[2-(3-indolyl)ethyl]-1-oxa-4,5-diazaspiro-[5.5]undecan-3-one and the pharmaceutically acceptable acid addition salts thereof.

7. A compound of claim 1 wherein R, $R^1$ and $R^2$ are independently hydrogen or lower alkyl of one to four carbon atoms and $R^3$, $R^4$, $R^5$, and $R^6$ are hydrogen.

8. A compound of claim 7 wherein $R^1$ is methyl and R and $R^2$ are each hydrogen which is 4-methyl-9-[2-(3-indolyl)ethyl]-1-oxa-4,9-diazaspiro-[5.5]undecan-3-one and the pharmaceutically acceptable acid addition salts thereof.

9. A compound of claim 7 wherein $R^1$ is ethyl and R and $R^2$ are each hydrogen which is 4-ethyl-9-[2-(3-indolyl)ethyl]-1-oxa-4,9-diazaspiro-[5.5]undecan-3-one and the pharmaceutically acceptable acid addition salts thereof.

10. A compound of claim 7 wherein R is methyl, $R^1$ is ethyl and $R^2$ is hydrogen which is 4-ethyl-5-methyl-9-[2-(3-indolyl)ethyl]-1-oxa-4,9-diazaspiro[5.5]undecan-3-one and the pharmaceutically acceptable acid addition salts thereof.

11. A compound of claim 7 wherein R is ethyl, $R^1$ is methyl and $R^2$ is hydrogen which is 4-methyl-5-ethyl-9-[2-(3-indolyl)ethyl]-1-oxa-4,9-diazaspiro[5.5]undecan-3-one and the pharmaceutically acceptable acid addition salts thereof.

12. A compound of claim 7 wherein $R^1$ is n-propyl and R and $R^2$ are each hydrogen which is 4-n-propyl-9-[2-(3-indolyl)ethyl]-1-oxa-4,9-diazaspiro[5.5]undecan-3-one and the pharmaceutically acceptable acid addition salts thereof.

13. A compound of claim 7 wherein R and $R^1$ are each methyl and $R^2$ is hydrogen which is 4,5-dimethyl-9-[2-(3-indolyl)ethyl]-1-oxa-4,9-diazaspiro[5.5]undecan-3-one and the pharmaceutically acceptable acid addition salts thereof.

14. A compound of claim 7 wherein $R^2$ is methyl and R and $R^1$ are each hydrogen which is 2-methyl-9-[2-(3-indolyl)ethyl]-1-oxa-4,9-diazaspiro-[5.5]undecan-3-one and the pharmaceutically acceptable acid addition salts thereof.

15. A compound of claim 7 wherein $R^2$ is ethyl and R and $R^1$ are each hydrogen which is 2-ethyl-9-[2-(3-indolyl)ethyl]-1-oxa-4,9-diazaspiro-[5.5]undecan-3-one and the pharmaceutically acceptable acid addition salts thereof.

16. A compound of claim 7 wherein $R^1$ and $R^2$ are each methyl and R is hydrogen which is 2,4-dimethyl-9-[2-(3-indolyl)ethyl]-1-oxa-4,9-diazospiro[5.5]undecan-3-one and the pharmaceutically acceptable acid addition salts thereof.

17. A compound of claim 7 wherein $R^1$ is methyl, $R^2$ is ethyl and R is hydrogen which is 2-ethyl-4-methyl-9-[2-(3-indolyl)ethyl]-1-oxa-4,9-diazaspiro[5.5]undecan-3-one and the pharmaceutically acceptable acid addition salts thereof.

18. A pharmaceutically composition comprising 5 to 95% by weight of a compound of the formula

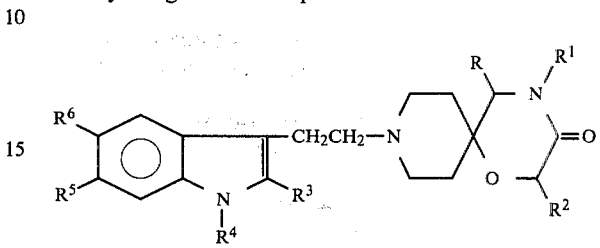

or a pharmaceutically acceptable acid addition salt thereof, wherein:

R, $R^1$, $R^2$, $R^3$, and $R^4$ are independently hydrogen, or lower alkyl of one to four carbon atoms;

$R^5$ and $R^6$ are independently hydrogen, lower alkyl of one to four carbon atoms or lower alkoxy of one to four carbon atoms; in admixture with 90 to 10% of a pharmaceutically acceptable, non-toxic carrier.

19. A method for treating and/or preventing hypertension, congestive heart failure, arrhythmia, migraine, vasospastic disorders and asthma in a mammalian subject comprising administering to said subject a therapeutically effective amount of a compound of the formula

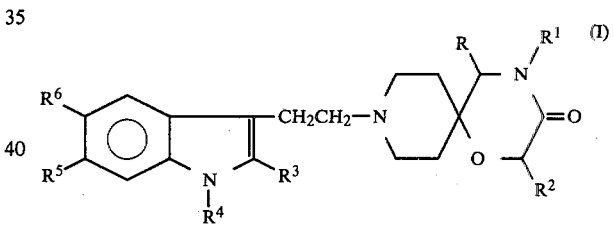

or a pharmaceutically acceptable acid addition salt thereof, wherein:

R, $R^1$, $R^2$, $R^3$, and $R^4$ are independently hydrogen or lower alkyl of one to four carbon atoms; and $R^5$ and $R^6$ are independently hydrogen, lower alkyl of one to four carbon atoms or lower alkoxy of one to four carbon atoms or a pharmaceutical composition containing such compound as an active ingredient.

20. A method of claim 19 for treating and/or preventing hypertension in a mammalian subject.